(12) United States Patent
Walker et al.

(10) Patent No.: US 6,256,524 B1
(45) Date of Patent: Jul. 3, 2001

(54) PULSE OXIMETER SENSOR COMBINED WITH A COMBINATION OROPHARYNGEAL AIRWAY AND BITE BLOCK

(75) Inventors: Steven C. Walker, Olmos Park; John M. Shepherd, Fort San Antonio; John G. Alexander, Plano, all of TX (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/389,355

(22) Filed: Sep. 3, 1999

Related U.S. Application Data

(60) Provisional application No. 60/101,079, filed on Sep. 18, 1998, and provisional application No. 60/099,579, filed on Sep. 9, 1998.

(51) Int. Cl.[7] .............................. A61B 5/00; A61M 16/00
(52) U.S. Cl. ................ 600/340; 128/200.26; 128/207.15
(58) Field of Search ................................ 600/310, 322, 600/323, 340, 344, 338–44; 128/200.26, 200.24, 203.13, 203.22, 204.18, 205.11, 207.18, 207.14, 207.15

(56) References Cited

U.S. PATENT DOCUMENTS

| | | |
|---|---|---|
| 2,669,988 | 2/1954 | Carpenter . |
| 2,882,893 | 4/1959 | Godfroy . |
| 3,908,665 | 9/1975 | Moses . |
| 4,112,936 | 9/1978 | Blachly . |
| 4,198,970 * | 4/1980 | Loumanen ........................ 128/207.15 |
| 4,270,531 | 6/1981 | Blachly, et al. . |
| 4,495,945 | 1/1985 | Liegner . |
| 4,586,513 | 5/1986 | Hamaguri . |
| 4,621,643 | 11/1986 | New, Jr. et al. . |
| 4,624,572 | 11/1986 | Van Den Bosch . |
| 4,651,746 | 3/1987 | Wall . |
| 4,676,240 | 6/1987 | Gardy . |
| 4,700,708 | 10/1987 | New, Jr. et al. . |
| 4,796,636 | 1/1989 | Branstetter et al. . |
| 4,830,014 | 5/1989 | Goodman et al. . |
| 4,854,699 | 8/1989 | Edgar, Jr. . |
| 4,859,057 | 8/1989 | Taylor et al. |
| 4,865,038 | 9/1989 | Rich et al. . . . |

(List continued on next page.)

FOREIGN PATENT DOCUMENTS

| | | |
|---|---|---|
| 4 42 260A1 | 5/1996 | (DE) . |
| WO 86/00207 | 1/1986 | (WO) . |

(List continued on next page.)

OTHER PUBLICATIONS

Hayes, et al., "Quantitative Investigation of Artefact in Photoplethysmography and Pulse Oximetry for Respiratory Exercise Testing," Aug. 27, 1998, Web Article: http://www.LUT.AC.UK/departments/EL/research/optics/PPGRAPHY/paper2c.htm.

(List continued on next page.)

*Primary Examiner*—Eric F. Winakur
(74) *Attorney, Agent, or Firm*—Elizabeth Arwine; Charles H. Harris

(57) ABSTRACT

A combined oropharyngeal airway/bite block is disclosed having pulse oximeter sensor elements capable of monitoring the posterior pharynx, the soft palate, the hard palate, and the buccal surface. The oropharyngeal airway portion has a thickened wall to house the pulse oximeter sensor elements and provide sufficient material to form grooves in the distal end. The grooves are utilized when the invention is turned on its side to act as a bite block with the grooves engaging the teeth of the patient. The pulse oximeter sensor elements include a light source, which emits light at wavelengths of about 660 nm and about 940 nm, and a light detector. The pulse oximeter sensor elements are in communication with a spectrophotometer for analysis.

37 Claims, 4 Drawing Sheets

U.S. PATENT DOCUMENTS

| | | |
|---|---|---|
| 4,867,557 | 9/1989 | Takatani et al. . |
| 4,880,304 | 11/1989 | Jaeb et al. . |
| 4,890,619 | 1/1990 | Hatschek . |
| 5,040,539 | 8/1991 | Schmitt et al. . |
| 5,069,214 | 12/1991 | Samaras et al. . |
| 5,090,410 | 2/1992 | Saper et al. . |
| 5,193,544 * | 3/1993 | Jaffe ..................................... 600/323 |
| 5,203,329 | 4/1993 | Takatani et al. . |
| 5,205,281 | 4/1993 | Buchanan . |
| 5,217,012 | 6/1993 | Young et al. . |
| 5,246,003 | 9/1993 | Delonzor . |
| 5,282,464 | 2/1994 | Brain . |
| 5,318,017 * | 6/1994 | Ellison ................................ 600/435 |
| 5,329,922 | 7/1994 | Atlee, III . |
| 5,355,874 | 10/1994 | Bertram . |
| 5,357,954 | 10/1994 | Shigezawa et al. . |
| 5,361,757 | 11/1994 | Smith et al. . |
| 5,413,101 | 5/1995 | Sugiura . |
| 5,417,207 | 5/1995 | Young et al. . |
| 5,494,032 | 2/1996 | Robinson et al. . |
| 5,595,176 | 1/1997 | Yamaura . |
| 5,596,986 | 1/1997 | Goldfarb . |
| 5,619,992 | 4/1997 | Guthrie et al. . |
| 5,638,593 | 6/1997 | Gerhardt et al. . |
| 5,655,519 | 8/1997 | Alfrey . |
| 5,673,693 | 10/1997 | Solenberger . |
| 5,678,544 | 10/1997 | Delonzor et al. . |
| 5,715,816 | 2/1998 | Mainiero et al. . |
| 5,743,261 | 4/1998 | Mainiero et al. . |
| 5,755,226 * | 5/1998 | Carim et al. .......................... 600/323 |
| 5,797,841 | 8/1998 | Delonzor et al. . |
| 5,800,349 | 9/1998 | Isaacson et al. . |
| 5,817,009 | 10/1998 | Rosenheimer et al. . |
| 5,839,439 | 11/1998 | Nierlich et al. . |
| 5,954,050 | 9/1999 | Christopher . |
| 5,983,120 | 11/1999 | Groner et al. . |
| 5,991,648 | 11/1999 | Levin . |

FOREIGN PATENT DOCUMENTS

| | | |
|---|---|---|
| WO 90/01293 | 2/1990 | (WO) . |
| WO 90/07907 | 7/1990 | (WO) . |
| WO 6/29927 | 10/1996 | (WO) . |
| WO 96/31155 | 10/1996 | (WO) . |
| WO 97/42903 | 11/1997 | (WO) . |

OTHER PUBLICATIONS

Anonymous, "Photon Flow For Pulse Oximetry," Sep. 15, 1995, Web Article: http://www.LLNL.gov/BBRP/health-care/projects/PFPULSEOXIM.html.

Heathgate Data Corp., "Pulse Oximetry," Jun. 13, 1997, Web Article: http://www.healthgate.com/healthgate/free/DPH/static/DPH.0200.shtml.

Jobes, et al., "Monitoring of Arterial Hemoglobin Oxygen Saturation Using a Tongue Sensor," Anesthesia & Analgesia, Feb., 1988, vol. 67, pp. 186–188.

O'Leary, et al., "Buccal Pulse Oximeter Is More Accurate Than Finger Pulse Oximeter in Measuring Oxygen Saturation," Anesthesia & Analgesia, Oct., 1992, vol. 75, pp. 495–498.

Cote, et al., "Tongue Oximetry in Children with Extensive Thermal Injury: Comparison with Peripheral Oximetry," Can. Journal Anaesth., May, 1992, vol. 39, Issue 5, pp. 454–457.

Reynolds, et al., "Influence of Sensor Site Location on Pulse Oximetry Kinetics in Children," Anesthesia & Analgesia, 1993, vol. 76, pp. 751–754.

Faisst, et al., "Reflectance Pulse Oximetry in Neonates," European Journal of Obstetrics & Gynecology and Reproductive Biology, Aug., 1995, vol. 61, pp. 117–122.

Sheridan et al., "Intraoperative Reflectance Oximetry in Burn Patients," Journal of Clinical Monitoring, Jan. 1995, vol. 11 (1): 32–34.

Faisst et al., "Intrapartum Reflectance Pulse Oximetry: Effects of Sensor Location and Fixation Duration on Oxygen Saturation Readings," Journal of Clinical Monitoring, Sep. 1997, vol. 13 (5): 299–302.

Izumi et al., "Accuracy and Utility of a New Reflectance Pulse Oximeter for Fetal Monitoring During Labor," Journal of Clinical Monitoring, Mar. 1997, vol. 13 (2): 103–108.

* cited by examiner

FIG. 9
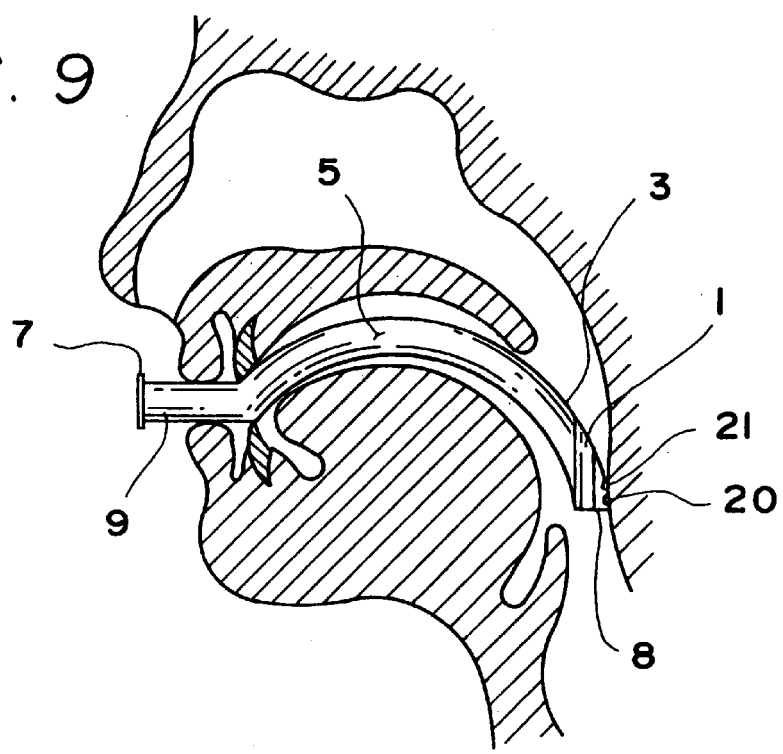
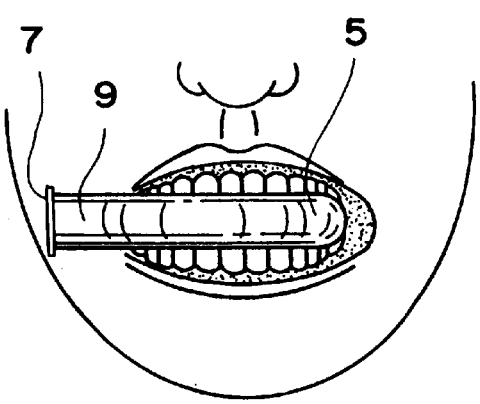
FIG. 10(a)
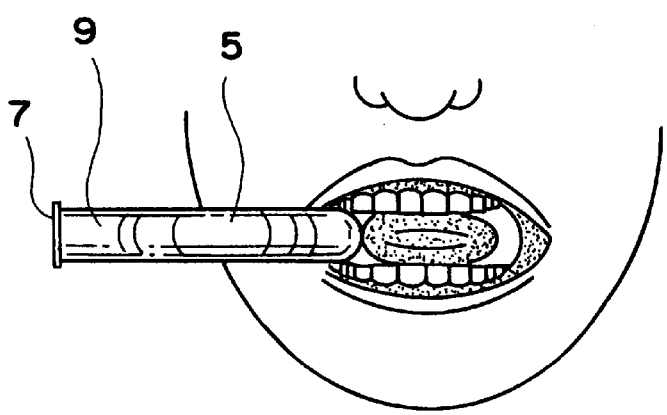
FIG. 10(b)

PULSE OXIMETER SENSOR COMBINED WITH A COMBINATION OROPHARYNGEAL AIRWAY AND BITE BLOCK

This application claims priority from U.S. provisional Application Ser. No. 60/099,579, filed Sep. 9, 1998 and U.S. provisional Application Ser. No. 60/101,079, filed Sep. 18, 1998.

FIELD OF THE INVENTION

The invention relates to a combination oropharyngeal airway and bite block with pulse oximetry capabilities. More particularly, the invention relates to a device that allows for intraoral application of pulse oximeter sensors to a patient while establishing a ventilatable airway for the patient and/or maintaining separation between the patient's upper and lower teeth.

BACKGROUND OF THE INVENTION

With a few exceptions, tradition and technology have favored transillumination pulse oximetry in the operating theater. The principle of operation of the pulse oximeter is fairly simple but is arguably the most important development in anesthesia monitoring in the twentieth century. Two wavelengths of light (usually 660 nm and 940 nm) are used to spectrophotometrically determine the ratio of oxidized to reduced hemoglobin noninvasively as well as to determine the pulsatility of blood plethysmographically. Presently, the most common application of this in the operating theater is via transillumination through the capillary bed of a peripheral digit. However, it is not unusual for multitrauma and thermally injured patients to either have severe peripheral vasoconstriction or to have severely damaged (or missing due to amputation) peripheral vascular beds. Reflectance oximetry rather than transillumination oximetry was the earliest investigative form of the technique. Transillumination pulse oximetry, without question, is the most effective form when oximetry is obtained through skin. However, when skin is not interposed as a barrier to capillary bed access, reflectance pulse oximetry easily can be achieved with very accurate results. The effect is achieved by the backscattering of incident bispectral light that traverses and, on reflection from nonabsorptive collagenous tissues, retraverses formed elements in the blood back to the oximetric detector. Rather than superseding transillumination pulse oximetry, this technique broadens the scope of possible monitoring sites, adding to the clinician's armamentarium.

Previously, three devices were needed to accomplish the functions provided by this invention. An oropharyngeal airway and a bite block are sold as two separate pieces that are used at different times and in different situations. A pulse oximeter sensor is used to take readings for the determination and measurement of oxygen saturation in the blood without taking a blood sample. Prior art devices have combined the oropharyngeal airway with the capability to perform transilluminance pulse oximetry through the posterior tongue or have placed oximeter sensors farther down the trachea then is proposed by this invention.

The oropharyngeal airway is used during surgical anesthesia. If the oropharyngeal airway is inserted prior to induction of anesthesia or left inserted upon emergence from anesthesia, then there is the possibility that the patient could be stimulated to vomit and aspirate stomach contents resulting in an often fatal event for the patient. Also, the oropharyngeal airway will cause uncomfortable stimulations deep in the throat and thus cause gagging and the impingement of the teeth upon the endotracheal tube prior to extubation if the patient awakens from anesthesia. Thus the oropharyngeal airway may not be inserted until the patient is profoundly sedated and must be removed once the patient begins to awaken. The oropharyngeal airway establishes a ventilatable airway in a patient who is unconscious.

The bite block maintains an oral aperture for suction and the passage of air or vomit. The bite block is also used to prevent biting of an endotracheal tube. The bite block does not stimulate the posterior tongue or pharynx.

Prior pulse oximeter sensors inserted through the mouth are usable only when the patient is under general anesthesia. These pulse oximeter sensors are inserted to reach the larynx area, for example, U.S. Pat. No. 5,282,464 to Brain et al. Another known method uses transillumination pulse oximetry of the posterior tongue, but this method may not be used with a patient, who is awake, for example, U.S. Pat. No. 5,205,281 to Buchanan. Also, the posterior tongue is not the most accessible body part to take oximetric measurements.

Conventional pulse oximetry in the severely burned patient can be a significant challenge, yet this monitoring data is vital in operating room and intensive care settings. Most current oximetric approaches depend upon available peripheral sites permitting transillumination oximetry and indeed, this method is sufficient for most surgical conditions and procedures. Unfortunately, patients with severe burns often have few sites for the effective placement of the transilluminating pulse oximeter sensor. In addition, these patients often have severe circulatory compromise rendering the peripheral pulse oximeter less efficient.

Recent studies indicate that oral pulse oximetry is a superior modality when compared to peripheral transillumination pulse oximetry. A variety of studies have shown that oral pulse oximeters are more reliably and rapidly responsive than peripheral pulse oximeters. However, these studies use oral transillumination pulse oximetry, held in place via complex devices or pieces of improvised malleable metal. Oral secretions, equipment failure, and placement difficulty often render these techniques ineffective.

Reflectance oximetry can be a useful tool where a capillary bed is easily accessible. Indeed, it is used commonly and effectively among intrapartum and neonatal patients whose capillary beds are easily accessed through their skin. The technique has also been applied to adult and pediatric burn patients by placing the reflectance sensor in wounds or over hyperemic sites such as healed partial thickness burns.

There are other often overlooked capillary beds readily accessible in most adult burn patients that are as amenable to reflectance oximetry as the forehead of the premature infant. The buccal surface, posterior soft palate, hard palate and proximal posterior pharynx of a burned patient are seldom compromised no matter how severe the burn, and the capillary beds are very close to the surface in those areas. Transillumination pulse oximetry of the tongue and cheek has been documented as a viable method of monitoring, but not everyone has the equipment available to place a transilluminating pulse oximeter on the tongue or cheek. A reflectance pulse oximeter has the bispectral emitter and the sensor in a side-by-side configuration rather than in opposition. The device may be placed flat upon a suitable capillary bed and it thus becomes a reflectance pulse oximeter. In this manner, a standard disposable finger pulse oximeter probe may simply be placed flat against the buccal surface, thus rendering it a reflectance rather than a transilluminating device.

Notwithstanding the usefulness of the above-described devices, and the above-identified recognized viability of transilluminating buccal pulse oximetry, a need exists for a more convenient device that combines a bite block with an oropharyngeal airway. Additional convenience is obtained by including a pulse oximeter sensor with a device that includes the bite block and the oropharyngeal airway.

SUMMARY OF THE INVENTION

This invention solves the ongoing problems of using multiple devices to perform intraoral oximetry measurements by providing a single device for performing such measurements. The invention while addressing the problems of the prior art obtains advantages that were not achievable with the prior art devices.

The invention encompasses a combined bite block and oropharyngeal airway in one device. In accordance with a second embodiment, the invention includes a pulse oximeter sensor with the combined bite block and oropharyngeal airway; thus achieving greater simplicity and convenience not possible when three separate devices were required to be on hand and used.

An object of this invention is to simplify the amount and type of medical devices that are required to be stocked by a medical facility or emergency crew.

Another object of the invention is to obtain a decrease in costs resulting from having one combination device instead of multiple devices.

Another object is the use of reflectance pulse oximetry in the oral cavity for a variety of field, emergency, surgical, anesthetic, or critical care procedures or situations to include patients that are awake, sedated or undergoing general anesthesia.

Still another object of the invention is to monitor oxygen levels in severely burned ICU patients who are difficult to monitor.

An advantage of the invention is an improvement in the quality of care resulting from elimination of the need to switch devices during the course of taking oximetry measurements.

Another advantage of the invention is that EMS crews and personnel will be able to use this invention easily in the field during emergency situations.

Another advantage of the invention is improved pulse oximetry readings.

Another advantage of the invention is reflectance pulse oximetry requires less power to function and thus less heat is produced, which decreases the risk the patient will be burned. If the patient is burned, then the blood flow and saliva production will facilitate regeneration of the capillary bed quicker than in other tissue areas.

The invention accomplishes the above objectives and achieves the advantages. The invention is easily adapted to a wide variety of situations.

Furthermore, intraoral (i.e., lingual, buccal or proximal posterior pharyngeal/palatal) placement of a disposable pulse oximeter probe in a configuration relying upon reflectance will provide pulse oximetry measurements comparable to those obtained by peripheral pulse oximetry. The invention and test data suggest that buccal and proximal posterior pharyngeal/palatal reflectance pulse oximetry provides a simple, accurate means of monitoring arterial oxygen saturation in the severely burned patient where oximetric monitoring presents a challenge.

Given the following enabling description of the drawings, the apparatus should become evident to a person of ordinary skill in the art.

DESCRIPTION OF THE DRAWINGS

FIG. 9 illustrates the embodiment shown in FIG. 5 in use as an oral airway.

FIGS. 10(*a*) and (*b*) illustrate the embodiment shown in FIG. 5 in use as a bite block.

DETAILED DESCRIPTION OF THE INVENTION

Figure 1:
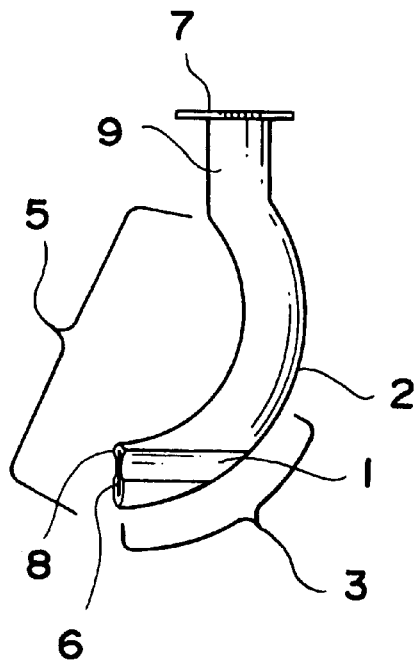
FIG. 1 illustrates a side view of a preferred embodiment.
Figure 2:
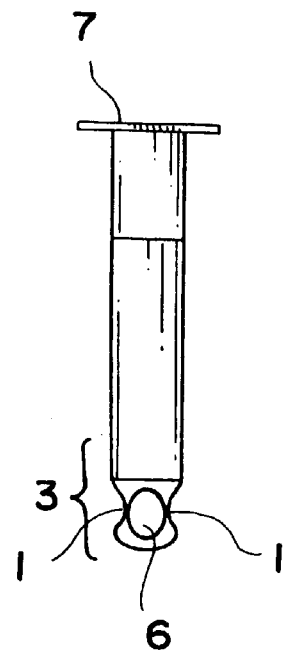
FIG. 2 illustrates a front view of the embodiment shown in FIG. 1.
Figure 3:
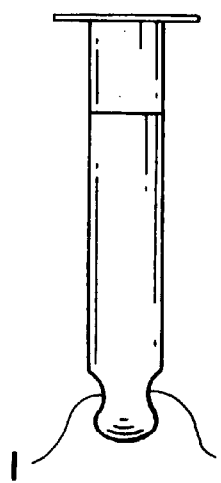
FIG. 3 illustrates a rear view of the embodiment shown in FIG. 1.
Figure 4:
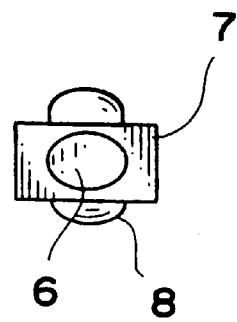
FIG. 4 illustrates a top view of the embodiment shown in FIG. 1.
Figure 5:
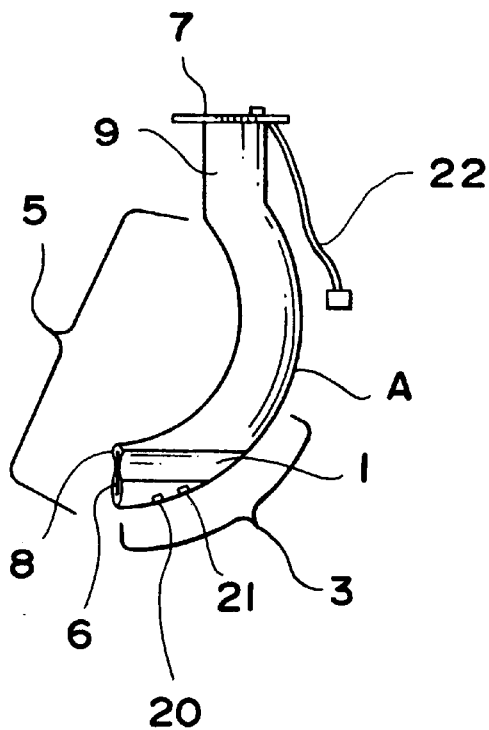
FIG. 5 illustrates a side view of another embodiment.
Figure 6:
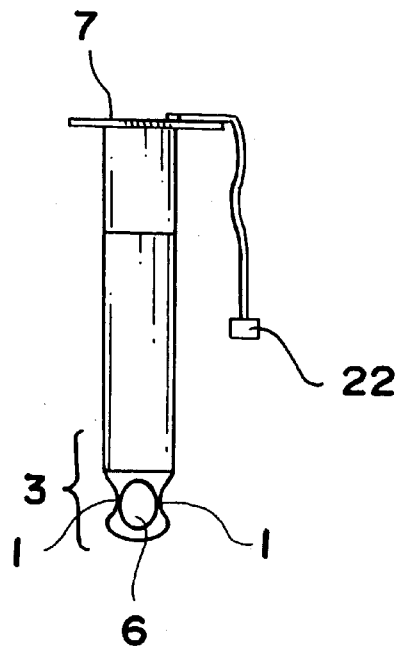
FIG. 6 illustrates a front view of the embodiment shown in FIG. 5.
Figure 7:
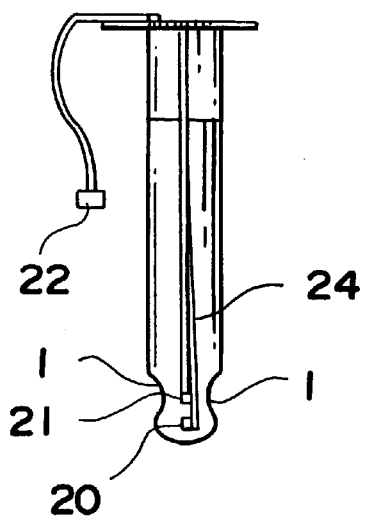
FIG. 7 illustrates a rear view of the embodiment shown in FIG. 5.
Figure 8:
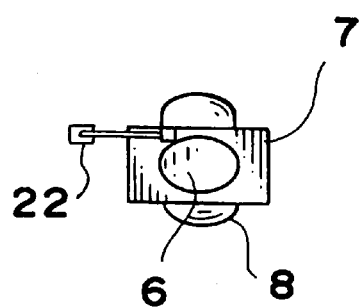
FIG. 8 illustrates a top view of the embodiment shown in FIG. 5.

FIGS. 1–4 illustrate an embodiment of the invention directed to a combination bite block and oropharyngeal airway. As depicted, the device includes a base 7, a straight portion 9, and a palatal and proximal pharyngeal contour portion 5 preferably arched to be physiologically compatible with the palate and pharynx. The contour portion 5 includes arched section 2 having an outer distal curve 3 and a distal end 8. The contour portion 5 is preferably integrally formed with straight portion 9, which includes a proximal end abutting the base 7. The base 7 preferably is large enough to allow the device to be manipulated by the user.

A central passageway or channel 6 may be formed within the device to extend from the distal end 8 to the base 7. As is apparent to one of ordinary skill in the art in view of the present disclosure, the cross-section and dimensions of the passageway 6 may be selected to maximize the airflow through the passageway without reducing the integrity of the device.

To facilitate operation of the device as a bite block, bilateral grooves (or recesses) 1 into which the teeth may fit are preferably disposed in opposing relationship to each other and formed in the contour portion 5. More preferably, the bilateral grooves extend from the distal end 8 to a point along the outer distal curve 3. The bilateral grooves 1 may be filled with a sponge-like or soft material, e.g., foam or rubber to protect the teeth. A significant advantage associated with this embodiment is that it may be employed as both a bite block and an oropharyngeal airway.

In accordance with a particularly advantageous feature of the invention, to accomplish a change between the two modes, the device only needs to be repositioned within the patient thus avoiding the need to exchange devices as required with present devices. For example, during anesthesia, it may be desirable to use the device as an oropharyngeal airway to establish a ventilatible airway for the patient. When used as such, the device is preferably inserted into the patient's mouth such that it impinges upon the posterior soft palate and/or the posterior pharynx along the outer distal curve 3.

In addition, before, on induction of, during, on emergence from and after anesthesia, it may be desirable to employ the device as a bite block. When used as such, the device is preferably inserted into the patients mouth such that the bilateral grooves 1 on the sides of the contour portion 5 may be inserted between the molars and/or bicuspids on one side of the mouth. The outer distal curve 3 in this mode abuts the buccal mucosa, as shown in FIG. 10(*a*). The alternative preferred insertion method is to place the device such that the bilateral grooves 1 are inserted between the molars and/or bicuspids on the side of the mouth that the base 7 is located. The outer distal curve 3 in this mode will abut the lingual surface of the tongue, as shown in FIG. 10(*b*). Neither mode will stimulate the posterior tongue/pharynx.

FIGS. 5–9 illustrate a second embodiment of the combination bite block and oropharyngeal airway that includes pulse oximeter sensor elements. This embodiment has the same basic structure as the previously described embodiment. In accordance with an aspect of the invention, pulse oximeter elements 20 and 21 reside in the posterior distal curvature of the device. The pulse oximeter elements 20 and 21 include a light source 20, which preferably emits light with wavelengths of 660 nm (red) and 940 nm (near infrared), and a light detector 21. The placement of the light source 20 and the light detector 21 may be switched with each other with respect to the placement shown in FIGS. 5, 7, and 9. Preferably, these pulse oximeter elements are embedded in the body of the device along the outer distal curve side 3 facing radially outward with a cover protecting them. Preferably the cover is a clear, fluid impermeable plastic. Alternatively, the pulse oximeter elements 20 and 21 may be disposed within passageway 6 adjacent the outer distal curve 3.

The light source 20 may include more than one emitter. The light source 20 is preferably one or more of the following: two light emitters such as light emitting diodes (LED), a bispectral emitter, a dual spectral emitter, a photoemitter, or a semiconductor die. However, any light source that facilitates reflectance pulse oximetry may be employed. When the light source 20 is one light emitter then the light emitter, for example, preferably would emit two frequencies of light at about 660 nm and about 940 nm. Typically, the two emitter arrangement will include a red LED near 660 nm and a near-infrared LED emitting in the range of 890 nm to 950 nm. The light source 20 may emit light having a bandwidth in the range of 20 nm to 50 nm.

A light detector 21 detects light emitted by light source 20. Electrical signals representing the detected light are transmitted by light detector 21 to a spectrophotometer or pulse oximeter that discriminates between the relative intensity of these emissions and provides an index as to the degree of oxygen saturation of hemoglobin in blood. Preferably, the light detector 21 may be one of the following: photoelectric receiver, photodetector, or a semiconductor die.

The pulse oximeter elements 20 and 21 may be disposed in a variety of locations along the passageway in accordance with the desired application. Preferably, the pulse oximeter elements 20 and 21 are placed closer to the distal end 8 of the device so that the readings may be taken from the post pharynx area, the buccal surface, or the lingual surface of the patient. As the pulse oximeter elements 20 and 21 are moved towards the apex of the arched section A, the readings more likely will be taken from the soft palate of the patient. The dividing line between these regions is highly dependent on the internal dimensions of the patient. However, the readings obtained from each area work equally well in terms of accuracy. Also, the closer to the apex of the arched section A the pulse oximeter elements 20 and 21 are, the more difficult it is for the device to contact the buccal surface or the lingual surface when the device is used as a bite block. When the pulse oximeter elements 20 and 21 are positioned away from the apex of the arched section A towards the proximal end abutting the base 7, the readings will be taken from the hard palate, which also will provide accurate pulse oximetry readings.

FIGS. 5–9 depict wiring 24 connecting the pulse oximeter elements to an external cord 22. Such wiring 24 is preferably also embedded in the body of the contour portion 5. The wiring 24 may include conductive lines and contact electrodes. The external cord 22 preferably is insulated and connects to the wiring 24 at the proximal end. The external cord 22 may include a standard plug designed to engage a pulse oximetry spectrophotometer or other external device. The spectrophotometer provides the electrical signals for controlling the pulse oximeter elements 20 and 21. Alternatively, pulse oximeter elements 20 and 21 may be in wireless communication with the pulse oximetry spectrophotometer or other external device.

As previously mentioned, the pulse oximeter elements may be disposed in the passageway. A disposable pulse oximeter sensor like the Nellcor® Oxisensor® II N-25 may be stripped of its surroundings to leave only the pulse oximeter elements. The pulse oximeter elements are then feed along the topside of the passageway 6. Although the pulse oximeter elements and wiring may be present in the passageway 6, there will be sufficient airflow capacity in the passageway to supply oxygen to the patient. The N-25 pulse oximeter sensor when installed in this manner does not overdrive as a result of the emitted brightness from the light source, because of the optical effects provided by the oropharyngeal airway.

To facilitate operation of the device as a pulse oximetry sensor, a plastic bag, protective cover or similar item may be placed around the distal end 8. This embodiment is particularly useful when there is excess moisture that might interfere with the operation of the pulse oximeter sensor elements.

Figure 11:
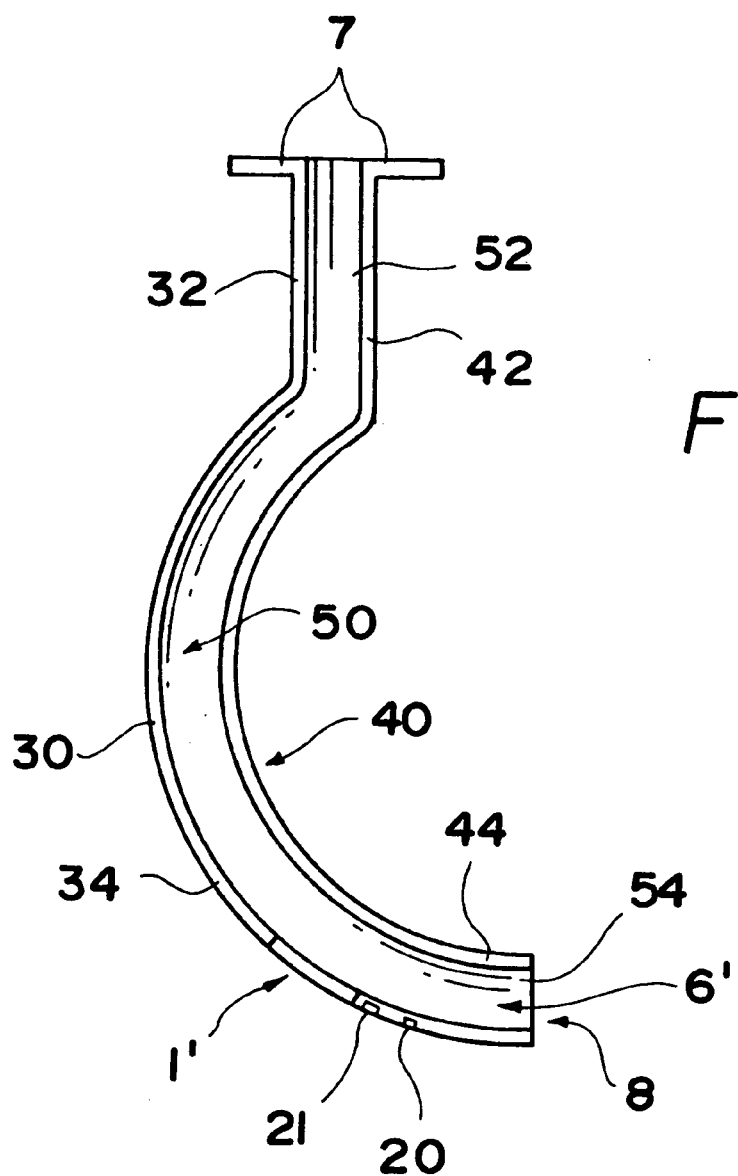
FIG. 11 illustrates a side view of another embodiment.
Figure 12:
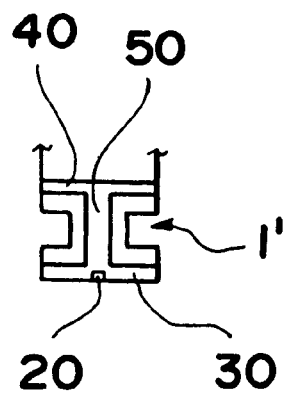
FIG. 12 illustrates a partial front view of the distal end of the embodiment shown in FIG. 11.

In accordance with an aspect of the invention, the passageway may have an I-beam construction as shown in FIGS. 11 and 12. The I-beam structure includes a first wall 30, a second wall 40, and a third wall 50. The first wall 30 runs parallel to the second wall 40 with the third wall 50 running perpendicular to and between the first two walls. Each wall preferably includes a straight portion 32, 42, and 52 and a distal curve portion 34, 44, and 54 configured to fit the contour of the palatal and proximal pharyngeal. At the end opposite the distal end 8 is a base 7. A passageway 6', as shown in FIG. 11, is formed on either side of the third wall 50 and is framed by the first and second walls 30 and 40. A groove 1' may be provided in the first wall 30 to provide a recess for the teeth to pass through to facilitate operation as a bite block.

Preferably, the pulse oximeter elements 20 and 21 are located within the first wall 30 in the distal curve portion 34. Preferably, the first wall 30 is thickened in the area around the pulse oximeter elements 20 and 21 slightly relative to the second wall 40 to better house the pulse oximeter elements 20 and 21. This area may include translucent material to allow for light to travel through the first wall 30. As one of ordinary skill in the art will appreciate, the pulse oximeter elements 20 and 21 may be placed within the third wall 50 in the distal curve portion 54 (not shown). The pulse oximeter elements 20 and 21 are positioned to perform reflectance pulse oximetry. The pulse oximeter elements 20 and 21 may be placed anywhere along the length of the first and third walls 30 and 50 in a manner similar to the previous embodiment. The wiring 24 connected to the pulse oximeter elements 20 and 21 preferably is within the same wall as the pulse oximeter elements 20 and 21. The wiring 24 may extend from the base 7 to connect to an external device.

When the device is used as the oropharyngeal airway, the pulse oximeter elements act as a reflectance pulse oximeter on the palate or proximal posterior pharynx. While in the case of the bite block, the pulse oximeter elements act as a reflectance pulse oximeter sensor on the buccal or lingual surfaces of the mouth depending on the orientation and placement of the device. Consequently, the pulse oximeter elements are able to act upon respective capillary beds to provide pulse oximetric data whether the patient is awake or under anesthesia.

The base oropharyngeal airway/bite block structure is preferably manufactured using polypropylene material that is either molded or extruded. Molding will produce a more rigid structure than extrusion. The sponge-like material, e.g., foam or rubber in the recesses may be added after forming the base oropharyngeal airway/bite block. Both molding and extrusion will allow the pulse oximeter sensor elements to be embedded in the oropharyngeal airway/bite block structure.

The invention may be used in a variety of surgical, anesthetic, combat or critical care procedures or situations that include patients that are awake, sedated or undergoing general anesthesia. In particular, the invention may be used throughout the pre-induction, induction, during, emergence from, and after anesthesia without switching devices. This advantage is accomplished while avoiding uncomfortable stimulation deep in the throat, which prevents gagging, vomiting, aspiration, and impingement of the teeth upon the endotracheal tube prior to extubation.

A method of taking pulse oximeter readings from different surfaces within a patient has been submitted to actual testing in the below-described population and according to the following protocols.

The first protocol involved taking readings from the buccal surface. Nine patients were monitored via buccal reflectance pulse oximetry over 20 consecutive surgical procedures, which procedures consisted of burn excision and grafting. Patients ranged in age from 23 to 56 years (Mean=34.8, Standard Deviation (SD)=11.2) and ranged from 17 to 75 percent total body surface area (%TBSA) burned (Mean=44.3%, SD=28.9). Each patient received from one to eight operations (Mean=4.01). Five of these nine patients arrived at the operating room intubated for all of the operations in this study. Four patients were induced and intubated in a standard fashion for all surgical procedures.

A Nellcor® Oxisensor® II D-25 (Nellcor Puritan Bennett®, Inc., Pleasanton, Calif.) was placed intraoraly between the lower teeth and the left or right buccal surface of the cheek and lip, with the bispectral emitter and sensor facing the buccal surface. This pulse oximeter orientation was used for the duration of each case. In addition, a similar disposable oximetric probe was placed on a peripheral digit in the commonly accepted transillumination configuration. At five minute intervals throughout the case, values for both oximetric probes were coded on the anesthesia record.

The differences between the peripheral and buccal $SpO_2$ (oxygen saturation of hemoglobin) values were insignificant by t-tests for correlated means. Concordance rates as percent agreements were calculated for all cases. Average percent agreement was 84% ranging from 25% to 100%. Three of the 20 samples had percent agreements less than 91%. In each of these cases, the peripheral pulse oximeter sensor appears to have failed, in two cases secondary to sepsis, and in another secondary to peripheral vasoconstriction in the face of a norepinepherine infusion. Buccal $SpO_2$ readings in all three cases continued to be 97% or greater.

This data suggests that buccal reflectance oximetry is a simple, accurate means of monitoring arterial oxygen saturation in the severely burned patient where oximetric monitoring presents a challenge. Given that central oximetry has been shown in numerous studies to be more rapidly responsive to oxygen saturation variability than peripheral oximetry, as well as more directly reflective of central oxygen saturation, there are few drawbacks and considerable benefit from this method. Indeed, in the three examples in this study where percent agreements were low, the peripheral oximetric probes were returning apparently erratic and/or generally low values while buccal oximetric readings remained at 97% or higher. All three of these patients had peripheral vascular compromise secondary to sepsis and/or a vasoconstricting agent (norepinepherine infusion).

It may appear from the study results, at first blush, that a full range of $SpO_2$ values was not tested and that the continuously high $SpO_2$ readings are spurious to the technique. On the contrary, in order to obtain a $SpO_2$ value greater or less than 85% a very specific set of relationships must be present relative to the bispectral emitter and light sensing oximetric elements. Thus, spuriously high values in particular do not consistently occur. High $SpO_2$ values require the presence of saturated hemoglobin. Unlike lingual oximetry, this technique is not necessarily limited to intubated patients as a flat disposable oximetric probe could be placed between the cheek and teeth of an awake patient. In addition to operating room considerations, ventilated patients in intensive care settings could benefit from this technique, especially given the more rapid response of a centrally placed pulse oximeter over a peripheral one.

The second protocol involved comparing posterior pharyngeal reflectance pulse oximetry to conventional peripheral transillumination pulse oximetry in difficult to monitor burn patients. Eight patients' records were reviewed over fourteen consecutive surgical procedures, all consisting of excision and grafting. Patients ranged in age from 9 to 43 years and ranged from 14.5% to 77.5% TBSA burned (Mean=30.4, SD=22.1). The number of operations per patient ranged from one to four.

A Nellcor® Oxisensor® II pulse oximeter probe was placed in the distal lumen of an appropriately sized oropharyngeal airway with sensor and emitter facing the posterior pharynx. A similar probe was placed on a peripheral digit as a transilluminating pulse oximeter. $SpO_2$ values were noted at five-minute intervals. Concordance statistics as well as a t-test for correlated means were calculated between the simultaneously obtained $SpO_2$ values.

The mean differences between pharyngeal reflectance and peripheral digital transillumination $SpO_2$ values were insignificant for all cases. Concordance statistics were as follows: 0.75 (n=1) and 1.0 (n=12).

Given the near perfect concordance statistics in this study, this data suggests that posterior pharyngeal reflectance oximetry is a simple, highly accurate means of monitoring arterial oxygen saturation in the severely burned patient where oximetric monitoring presents a challenge.

The third protocol involved taking readings from the lingual surface. Data was reviewed for eight difficult to monitor patients who were monitored via lingual reflectance pulse oximetry over twenty-five consecutive surgical procedures, all consisting of burn excision and grafting. Patients ranged in age from 26 to 57 years (Mean=36.0, SD=10.3). Patients ranged from 20% to 92% TBSA burned (Mean=66.75%, SD=26.42). Number of operations per patient ranged from one to five (Mean=3.13, SD=1.55). Six of these eight patients arrived to the operating room intubated for all of the operations in this study. Two patients were induced and intubated in a standard fashion.

In each case, a Nellcor® Oxisensor® II D-25 was centered flat on the superior lingual surface with sensor and bispectral emitter facing the lingual surface. This pulse oximeter configuration was used for the duration of each case. When clinically indicated, an arterial blood gas (ABG) sample was drawn and the $SpO_2$ noted for clinical monitoring and prior to transfusion in every case. All had multiple ABG's drawn and all patients were transfused. The ABG $SaO_2$ (oxygen saturation of arterial blood) was noted in each case.

Descriptive statistics and a concordance rate as well as a t-test for correlated means were calculated between the simultaneously obtained $SpO_2$ and $SaO_2$ values. The difference between the $SpO_2$ and $SaO_2$ values was insignificant by t-test for correlated means (t=1.25, df=24, NS). Upon inspection, the means were very close and the standard deviations were very small as were the SEM's, all suggesting very little difference or variability between these two measures of oxygen saturation. A concordance rate of 92% was calculated (+1.5%) showing a high degree of relationship between lingual and ABG $SaO_2$.

This data suggests that lingual reflectance oximetry is a simple, accurate means of monitoring arterial oxygen saturation in the severely burned patient where oximetric monitoring presents a challenge. An existing disposable pulse oximeter was utilized in this study saving the cost of specially designed equipment. Given that central oximetry has been shown to be more rapidly responsive to oxygen saturation variability than peripheral oximetry, there are few drawbacks and considerable benefit from this method. One drawback is that the technique is probably limited to intubated patients, as awake, extubated patients could find the presence of a lingual pulse oximeter irritating. However, this limitation would hold with lingual transillumination pulse oximetry as well. In addition to operating room considerations, ventilated patients in intensive care settings could benefit from this technique, especially given the more rapid response of a centrally placed pulse oximeter over a peripheral one.

Those skilled in the art will appreciate that various adaptations and modifications of the above-described preferred embodiments can be configured without departing from the scope and spirit of the invention. Therefore, it is to be understood that, within the scope of the appended claims, the invention may be practiced and constructed other than as specifically described herein.

What is claimed is:

1. An intraoral device comprising:
   a base having a hole passing therethrough, and
   a conduit extending from said base, said conduit including
      a straight portion and a distal curve portion configured to substantially match a palatal and proximal pharyngeal contour of a patient, said distal curve portion having a distal end, an outer distal curve, and at least one straight recess extending along an outside of said conduit from said distal end to a point along said outer distal curve spaced from said distal end, said distal end having a hole passing therethrough, said conduit having a passageway in communication with the hole in said base and the hole in said distal end; and
   wherein said at least one straight recess is for engaging the teeth of a patient.

2. The intraoral device as recited in claim 1, further comprising:
   means for transmitting light at an intraoral tissue, and
   means for receiving light reflected from the intraoral tissue.

3. The intraoral device as recited in claim 2, wherein said means for transmitting and said means for receiving are embedded in said outer distal curve.

4. The intraoral device as recited in claim 2, wherein said means for transmitting and said means for receiving are disposed in the passageway.

5. The intraoral device as recited in claim 2, wherein said means for transmitting includes one of at least one light emitter, a bispectral emitter, a dual spectral emitter, at least one photoemitter, at least one photodiode, at least one light emitting diode, and a semiconductor die.

6. The intraoral device as recited in claim 1, wherein said at least one recess is filled with a flexible material.

7. The intraoral device as recited in claim 6, wherein the flexible material includes one of rubber, sponge and foam.

8. The intraoral device as recited in claim 1, further comprising:
   at least one light source, and
   at least one light detector in communication with said at least one light source.

9. The intraoral device as recited in claim 8, wherein said light source includes one of at least one light emitter, a bispectral emitter, a dual spectral emitter, at least one photoemitter, at least one photodiode, at least one light emitting diode, and a semiconductor die.

10. The intraoral device as recited in claim 9, wherein said light detector includes one of a photoelectric receiver, a photodetector, a photodiode receiver, and a semiconductor die.

11. The intraoral device as recited in claim 8, wherein said light source and said light detector are spaced along the outer distal curve such that light emitted from said light source that is backscattered is received eceived by said light detector.

12. The intraoral device as recited in claim 11, wherein said light source and said light detector are disposed near the distal end of the outer distal curve.

13. The intraoral device as recited in claim 11, wherein said light source and said light detector are disposed near an apex of the outer distal curve.

14. The intraoral device as recited in claim 11, wherein said light source and said light detector are disposed near a proximal end of the outer distal curve.

15. The intraoral device as recited in claim 8, wherein said light source and said light detector are embedded within said conduit.

16. The intraoral device as recited in claim 8, wherein said light source and said light detector are disposed in the passageway.

17. An intraoral reflectance pulse oximetry device comprising:
   a structural member having a first wall, a second wall disposed parallel to said first wall, and a third wall between and connecting said first wall and said second wall such that two opposing channels are formed to each other, each of said walls including a straight portion and a distal curve portion configured to substantially match a palatal and proximal pharyngeal contour of a patient, said distal curve portion having a distal end and an outer distal curve, a base attached to said structural member, pulse oximetry sensor elements disposed in said structural member including at least one light source housed within said structural member and at least one light detector housed within said structural member; and wherein said at least one light source and said at least one light detector are arranged to perform reflectance pulse oximetry.

18. The intraoral reflectance pulse oximetry device as recited in claim 17, wherein the light source includes one of at least one light emitter, a bispectral emitter, a dual spectral emitter, at least one photoemitter, at least one photodiode, at least one light emitting diode, and a semiconductor die.

19. The intraoral reflectance pulse oximetry device as recited in claim 18, wherein said light detector includes one of a photoelectric receiver, a photodetector, a photodiode receiver, and a semiconductor die.

20. The intraoral reflectance pulse oximetry device as recited in claim 19, wherein said light source and said light detector are spaced along the outer distal curve such that light emitted from said light source that is backscattered is received by said light detector.

21. The intraoral reflectance pulse oximetry device as recited in claim 19, wherein said first wall is thicker than said second wall, and said light source and said light detector are housed within said first wall.

22. The intraoral reflectance pulse oximetry device as recited in claim 21, wherein said light source and said light detector are disposed adjacent the distal end of said distal curve portion of said first wall.

23. The intraoral reflectance pulse oximetry device as recited in claim 21, wherein said light source and said light detector are disposed proximate to an apex of said distal curve portion of said first wall.

24. The intraoral reflectance pulse oximetry device as recited in claim 21, wherein said light source and said light detector are disposed adjacent to a proximal end of said distal curve portion of said first wall.

25. The intraoral reflectance pulse oximetry device as recited in claim 19, wherein said light source and said light detector are housed within said third wall.

26. The intraoral reflectance pulse oximetry device as recited in claim 25, wherein said light source and said light detector are disposed adjacent the distal end of said distal curve portion of said third wall.

27. The intraoral reflectance pulse oximetry device as recited in claim 25, wherein said light source and said light detector are disposed proximate to an apex of said distal curve portion of said third wall.

28. The intraoral reflectance pulse oximetry device as recited in claim 25, wherein said light source and said light detector are disposed adjacent to a proximal end of said distal curve portion of said third wall.

29. An intraoral device for performing reflectance pulse oximetry comprising:

a base having a hole passing therethrough, a conduit extending from said base, said conduit including a straight portion and a distal curve portion configured to substantially match a palatal and proximal pharyngeal contour of a patient, said distal curve portion having a distal end and an outer distal curve, said distal end having a hole passing therethrough, at least one light source, and at least one light detector in communication with said at least one light source and spaced from said at least one light source along said conduit; and wherein said at least one light source and said at least one light detector are arranged to perform reflectance pulse oximetry.

30. The intraoral device as recited in claim 29, wherein said light source includes one of at least one light emitter, a bispectral emitter, a dual spectral emitter, at least one photoemitter, at least one photodiode, at least one light emitting diode, and a semiconductor die.

31. The intraoral device as recited in claim 30, wherein said light detector includes one of a photoelectric receiver, a photodetector, a photodiode receiver, and a semiconductor die.

32. The intraoral device as recited in claim 29, wherein said light source and said light detector are spaced along the outer distal curve such that light emitted from said light source that is backscattered is received by said light detector.

33. The intraoral device as recited in claim 32, wherein said light source and said light detector are disposed near the distal end of the outer distal curve.

34. The intraoral device as recited in claim 32, wherein said light source and said light detector are disposed near an apex of the outer distal curve.

35. The intraoral device as recited in claim 32, wherein said light source and said light detector are disposed near a proximal end of the outer distal curve.

36. The intraoral device as recited in claim 29, wherein said light source and said light detector are embedded within said conduit.

37. The intraoral device as recited in claim 29, wherein said light source and said light detector are disposed in the passageway.

* * * * *